United States Patent
Norton-Wayne et al.

[11] Patent Number: 5,283,443
[45] Date of Patent: Feb. 1, 1994

[54] METHOD FOR INSPECTING GARMENTS FOR HOLES HAVING A CONTRASTING BACKGROUND

[75] Inventors: Leonard Norton-Wayne; Siavash Abbaszadeh, both of Leicester, Great Britain

[73] Assignee: De Montfort University, Leicester, United Kingdom

[21] Appl. No.: 937,872
[22] PCT Filed: Apr. 5, 1991
[86] PCT No.: PCT/GB91/00536
   § 371 Date: Dec. 3, 1992
   § 102(e) Date: Dec. 3, 1992
[87] PCT Pub. No.: WO92/08967
   PCT Pub. Date: May 29, 1992

[30] Foreign Application Priority Data
   Apr. 17, 1990 [GB] United Kingdom ............ 9008632

[51] Int. Cl.$^5$ ........................................... G01N 21/88
[52] U.S. Cl. ........................................ 250/572; 382/48
[58] Field of Search ................. 250/572, 562, 563; 356/392, 393, 394; 358/106, 107; 382/48, 51, 55, 8, 44, 45, 46

[56] References Cited

U.S. PATENT DOCUMENTS

| | | |
|---|---|---|
| 4,124,300 | 11/1978 | Mead et al. |
| 4,327,375 | 4/1982 | LeClerc |
| 4,330,712 | 5/1982 | Yoshida ............... 250/572 |
| 4,455,086 | 6/1984 | West et al. ............ 250/572 |
| 4,810,895 | 3/1989 | Kafri et al. ........... 250/572 |
| 4,900,153 | 2/1990 | Weber et al. |
| 4,952,062 | 8/1990 | Bean, III et al. |

FOREIGN PATENT DOCUMENTS

| | | |
|---|---|---|
| 0048568 | 3/1982 | European Pat. Off. |
| 0058028 | 8/1982 | European Pat. Off. |
| 0329889 | 8/1989 | European Pat. Off. |
| 0363177 | 4/1990 | European Pat. Off. |
| 3640851 | 6/1987 | Fed. Rep. of Germany |
| WO89/04887 | 6/1989 | PCT Int'l Appl. |
| WO90/12281 | 10/1990 | PCT Int'l Appl. |
| WO92/03721 | 3/1992 | PCT Int'l Appl. |
| WO92/08967 | 5/1992 | PCT Int'l Appl. |
| 2144219 | 2/1985 | United Kingdom |
| 2181834 | 4/1987 | United Kingdom |
| 2186365 | 8/1987 | United Kingdom |

OTHER PUBLICATIONS

Computers in Industry vol. 7, No. 2, Apr. 86, Amsterdam, NL, M. A. Sid-Ahmed: 'Specific Applications of image processing to surface flaw detection', see abstract, see p. 135, right column, line 3–p. 136 left column, line 11, see p. 137, left column, line 13–line 27, see p. 137, right column, section, 5.1, see FIGS. 5, 8.

Transactions of the Institute of Measurement and Control. vol. 10, No. 5, Dec. 1988, Dorking GB pp. 265–272; G. A. W. West: 'Image processing and understanding for automatic inspection' see p. 267, left column, line 9—line 19 see p. 267, right column, paragraph 4–p. 268, left column, line 42 see FIGS. 1–3.

NEC Research and Development No. 77, Apr. 1985, Tokyo JP pp. 93–102; S. Aratoh: 'Development of automatic digitizing system for PWB' see p. 99, line 9–line 17; FIG. 12D.

*Primary Examiner*—David C. Nelms
*Assistant Examiner*—Que T. Le
*Attorney, Agent, or Firm*—Oblon, Spivak, McClelland, Maier & Neustadt

[57] ABSTRACT

A method for inspecting garments for holes includes front-lighting the garment against a contrasting background and forming a pixel image thereof, isolating garment pixels from background pixels by automatically selecting an optimum binarization threshold grey level, binarizing the image at that level, determining the garment boundary, testing for consistency of grey level within the garment boundary on the binarized image along rows and columns of pixels within the garment boundary and noting inconsistent pixels, and identifying as holes only pixels which have been noted as inconsistent in both horizontal and vertical tests.

11 Claims, 6 Drawing Sheets

METHOD FOR INSPECTING GARMENTS FOR HOLES HAVING A CONTRASTING BACKGROUND

BACKGROUND OF THE INVENTION

This invention relates to inspecting garments for holes.

DISCUSSION OF THE BACKGROUND

Knitted garments, such as socks, are inspected during their production to reject any with faults. A principal fault in knitting is a hole, which may result from one of a number of reasons. Socks are best inspected at the boarding stage, where they are pulled on to a foot-shaped board for a setting treatment. Inspection is very labor-intensive, accounting for many more man-hours than the actual production of the socks, and is therefore a major cost area.

SUMMARY OF THE INVENTION

Moreover, inspectors become fatigued and can miss faults, so that imperfect socks—and other garments—can reach the customer.

The present invention provides an automatic procedure for inspecting garments, especially knitted garments such as socks, for any holes therein, which can be carried out quickly, using low-capital-cost equipment, during the normal manufacturing procedure and without requiring any additional handling operation.

The invention comprises a method for inspecting garments for holes comprising front-lighting the garment against a contrasting background and forming a pixel image thereof, isolating garment pixels from background pixels by automatically selecting an optimum binarization threshold grey level, binarizing the image at that level, determining the garment boundary, testing for inconsistency of grey level within the garment boundary on the binarized image along rows and columns of pixels within the garment boundary and noting inconsistent pixels, and identifying as holes only pixels which have been noted as inconsistent in both horizontal and vertical tests.

The threshold grey level may be selected on the basis of data from a part of the image, for example a single row or column of pixels.

The threshold grey level may be selected by thresholding the image (or the part of the image) at all possible grey levels to yield a histogram in which the number of segmented pixels is plotted against the threshold grey level, which histogram has two peak values, corresponding to object and background, and taking the optimum binarization threshold grey level to be that level at which the histogram has a minimum value between the peaks.

The garment boundary in the binarized image may be determined by tracing the boundary with an eight-directional Freeman chain code robot.

The determined garment boundary length may be compared to a predetermined minimum length to eliminate spurious measurements of noise clusters in the background.

The grey level consistency test may be carried out on a fresh, binarized image produced using a low pass filter operation on the original pixel image, that filtered image being binarized using the selected threshold grey level.

Any inconsistent pixel group discovered by the consistency test within the garment boundary may be indicated on a displayed image by a superimposed marker.

The pixel image may be made by a video camera or CCD device.

The garment may be a knitted garment such as a sock and may be carried out on the boarded garment.

A method for inspecting garments according to the invention will now be described with reference to the accompanying drawings, in which:

DESCRIPTION OF THE PREFERRED EMBODIMENTS

The drawings illustrate a method, carried out here on a knitted sock, for inspecting garments for holes.

Figure 1:
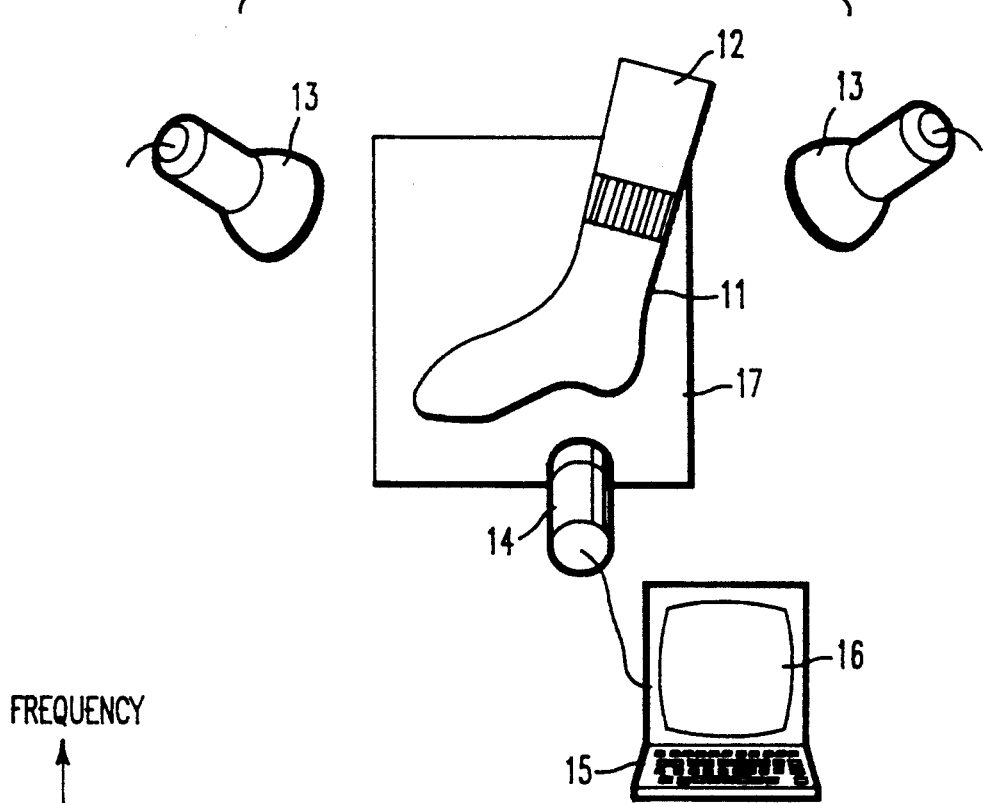
FIG. 1 is an illustration of an inspection arrangement.

FIG. 1 illustrates the equipment used in the method. The sock 11, placed on a board 12 for the conventional boarding operation, is front-lit by lamps 13 and viewed by a video camera or CCD device 14. Clearly, both sides of the sock 11 have to be imaged and the images processed in turn. The camera or CCD device 14 is connected to a computer 15 with a VDU 16 on which the images of FIGS. 3, 5 and 7-9 are displayed.

The marking of a hole fault on the displayed image may be accompanied by an audible warning to draw an inspector's attention to the fault so that the faulty sock can be picked out and discarded. Or an automatic arrangement may be actuated, which can be implemented in any of a variety of ways that will readily occur to engineers, to remove the sock from the line without human intervention.

While normally, the color of the board 12 is immaterial, in the present method it is desirable that it contrasts with the sock. However, in general it will be found that any sock will be sufficiently contrasted to a white or a black board, so only these two colors will normally be required. The choice of background 17 against which the boarded sock is viewed is made in a similar fashion.

It should at this juncture be noted not only that socks are produced in a wealth of colors, but also that they can be classified as plain or patterned. Even plain socks have regions of different texture. The welt usually has a rib texture, and the leg and foot will be of different textures. The method ignores these different textures and in large measure will also ignore most patterns, though it is possible to imagine patterns which would create difficulties in operating the method—the wise knitter will clearly avoid producing such patterns, or will at least inspect them in some other way.

Plain socks, and socks with untroublesome patterns predominate, however.

The video camera or CCD device 14 output—a stream of voltage signals for brightness or grey levels of the pixels—is digitized to produce a two-dimensional array of binary numbers representative of those voltage levels in a memory of the computer 15—this, in effect, is the raw image data. While a VDU is incorporated, in the equipment as illustrated it should be pointed out that in practice it may be unnecessary to view the image at any stage and indeed a visual image need never be produced if there is some other kind of warning or automatic discarding mechanism. The term "image" must therefore be understood in this light.

If the digitized brightness values are eight-bit bytes, there are 256 possible brightness or grey levels in the image from 0 (black) to 255 (white).

Figure 3:
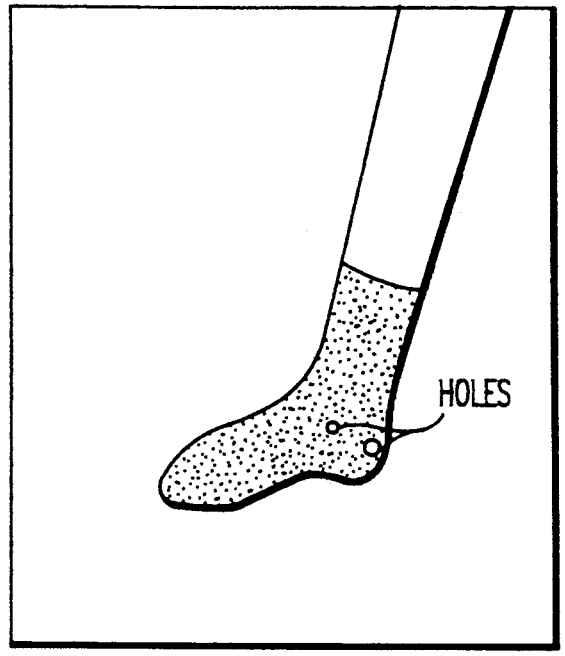
FIG. 3 is a primary pixel image of a sock.

The primary or raw image, if displayed at this stage on the VDU 16, would appear as shown in FIG. 3 where two holes can be made out. It is of course quite easy to spot these holes in the VDU image. The purpose of the following operations is to make the computer "recognize" that the holes are there.

The first step is to select an optimum binarization threshold grey level, so that all the pixels at that grey level, or darker, can be separated from all those that are lighter. The darker pixels can then all be adjusted to the same dark grey level (or black) while the others can be set to the same light grey (or white).

Figure 4:
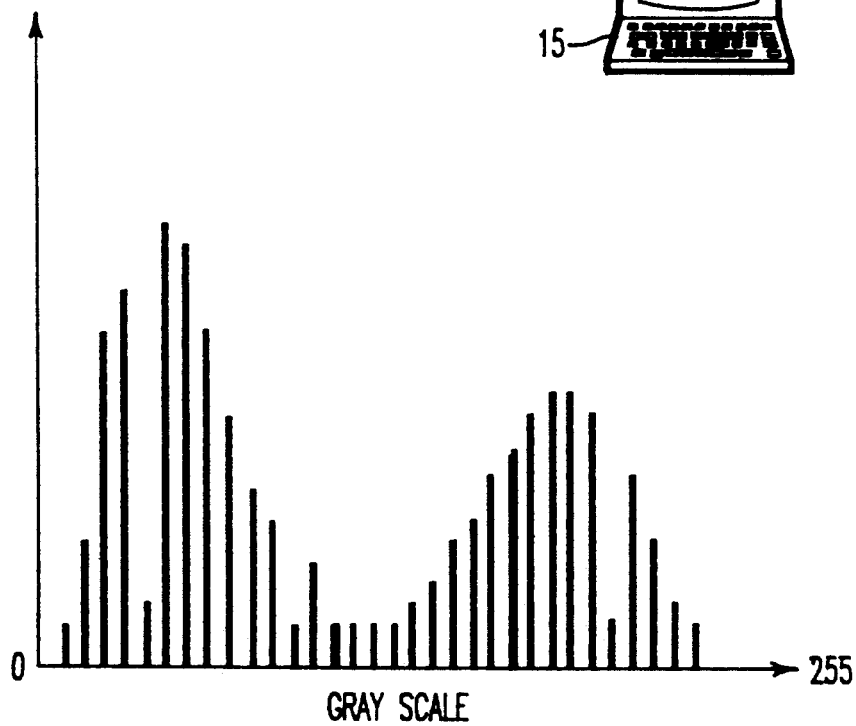
FIG. 4 is a histogram produced from the image of FIG. 3.
Figure 2:
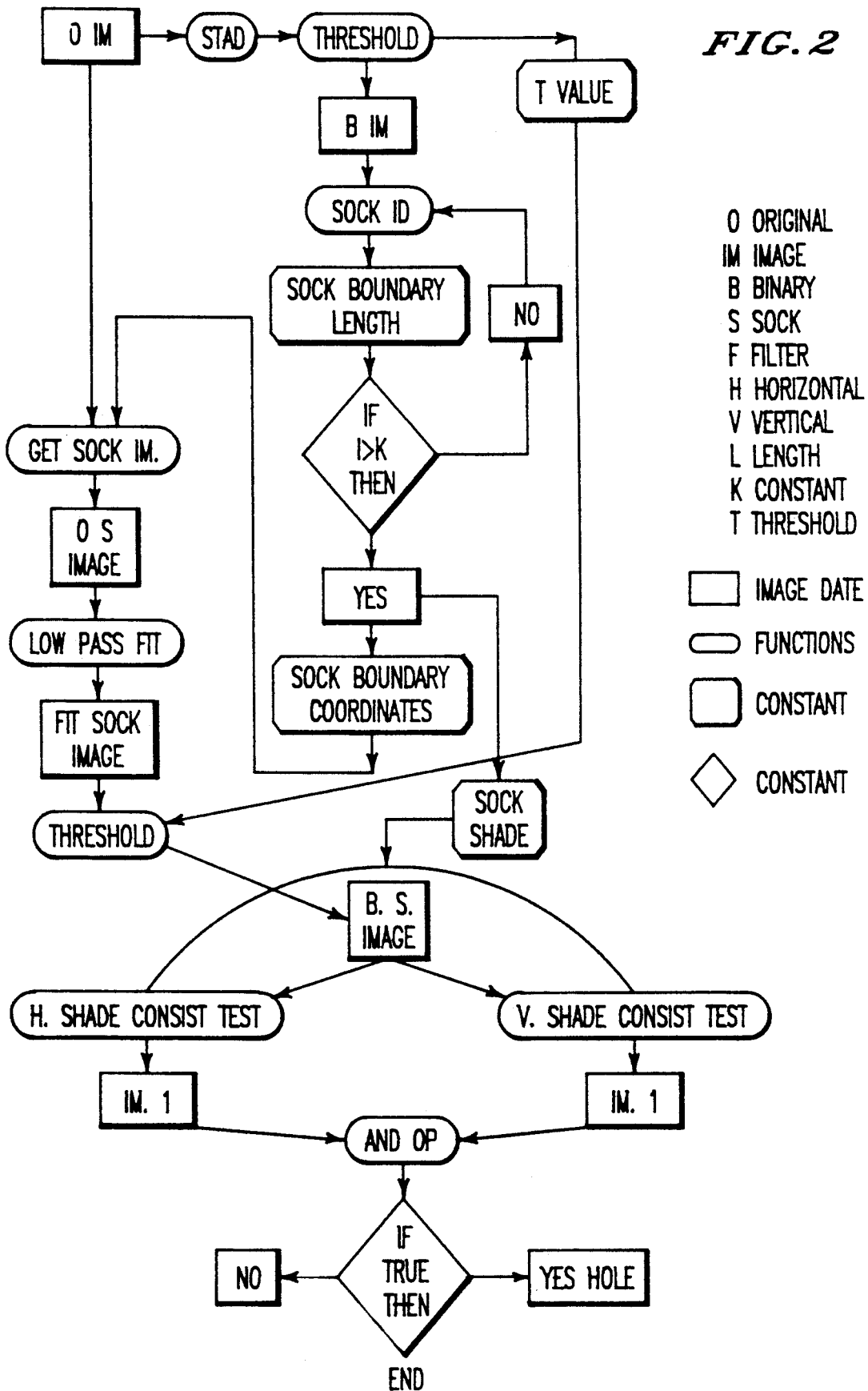
FIG. 2 is a flowchart.

Differences in lighting conditions, and colors and surface textures of socks presented for inspection, render the task of threshold grey level selection non-trivial. The task is achieved as follows:

(i) a line of the image is selected which has sock pixels and background pixels—in practice, a line half way down the image will normally have a representative selection of pixels, (ii) the pixels of this line are thresholded at all possible grey scale levels, i.e. 0 to 255 and a histogram plotted, as FIG. 4. It will be observed that the histogram has two peaks, one corresponding to background levels, the other to object levels. In between the two peaks is a minimum.

(iii) this minimum is located and its grey level selected as the optimum threshold level.

It will be appreciated that the above is a graphical description of processes that can be carried out purely computationally by the computer 15. There is no need in fact actually to plot the histogram on graph paper—where plotting is referred to herein, it is to be understood as a notional plotting carried on in the memory and logic circuits of the computer.

Figure 5:
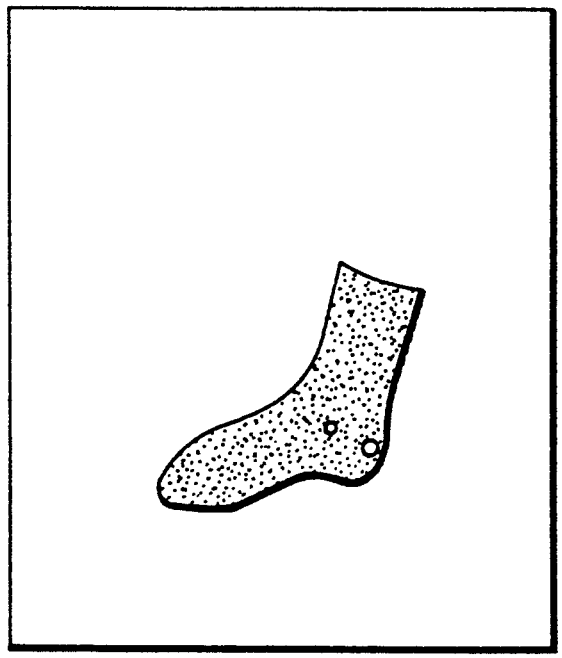
FIG. 5 is a segmented image.
Figure 6:
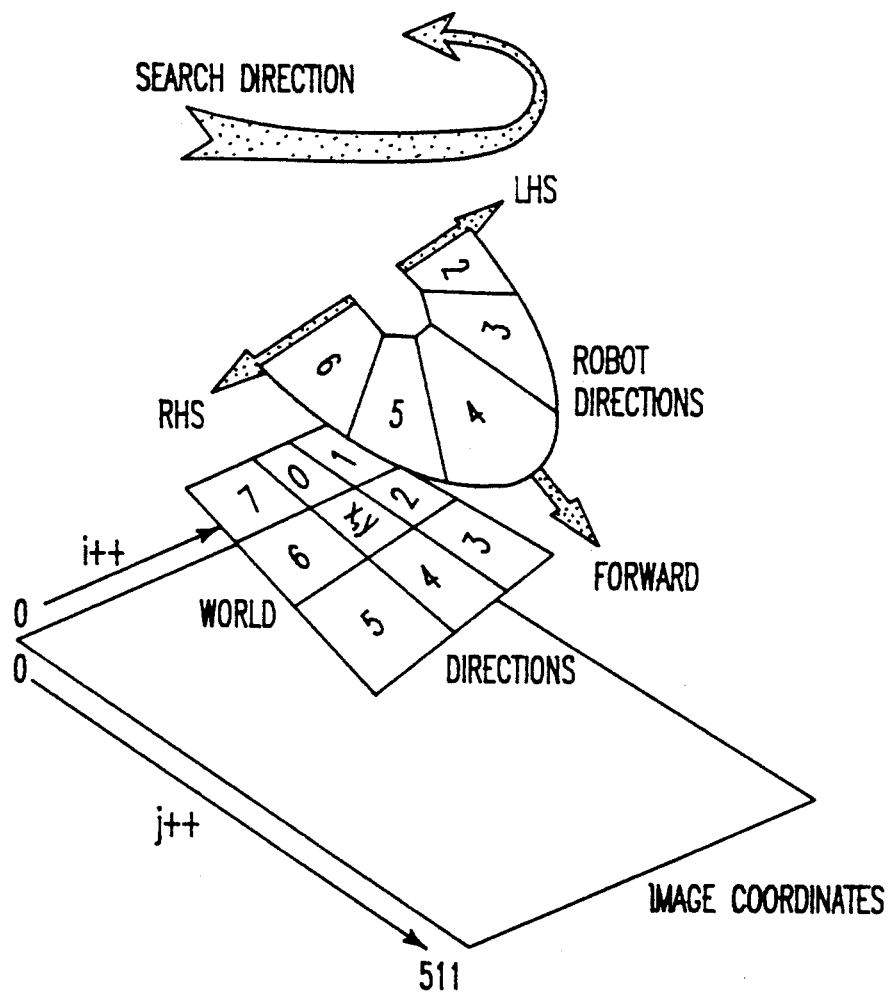
FIG. 6 is a diagrammatic representation of a Freeman chaincode boundary tracing operation.

The next step is that the raw image is binarized at the selected threshold level; the result of this process is an image as seen in FIG. 5 which has pixels at one or the other of two grey scale levels. This image is then used to determine the boundary of the image of the sock. This is done by an eight-directional Freeman chain code procedure as illustrated in FIG. 4. A "robot" tracer consisting of a 3×3 pixel cursor is set free from an edge of the image to move forward to the first available object point on its right hand side. The "forward" direction and "right hand side" are defined by numbering the pixels of the tracer. By comparing the relationships between the grey levels encountered by the various pixels of the tracer with those on the next move forward, it can be determined whether the forward move was to another point on the boundary or not. In this way, the tracer stays on and moves around the boundary, and each boundary point so located is saved as such into a buffer chain. The chain length is noted.

It is still possible at this stage that one or more clusters of "image" level pixels may be present in the background due to noise, and hence it is also possible that the robot will first encounter such a cluster and trace out its boundary. The saved chain length is, for that reason, compared with a constant, say, 800. If it is less than 800, it is assumed that the image traced was too small to be the garment, and the robot is moved to another position to start its search again.

Once the boundary has been identified, a new image is made from the originally-captured image by a low pass filtering technique to eliminate high frequency component noise. A suitable filtering technique is to average the grey level of each adjacent 3×3 pixel area and substitute the average value for the actual pixel grey level values. The resulting image is then binarized using the threshold value already selected as desired above.

Figure 7:
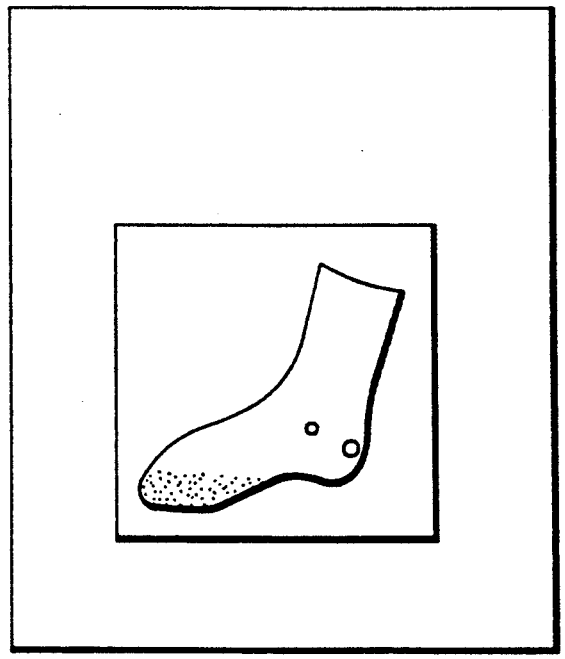
FIG. 7 is an image undergoing a horizontal consistency test.
Figure 8:
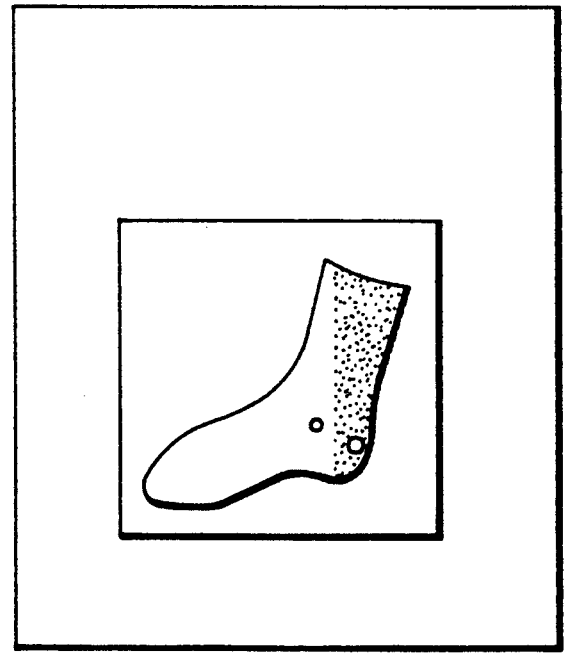
FIG. 8 is an image undergoing a vertical consistency test.
Figure 9:
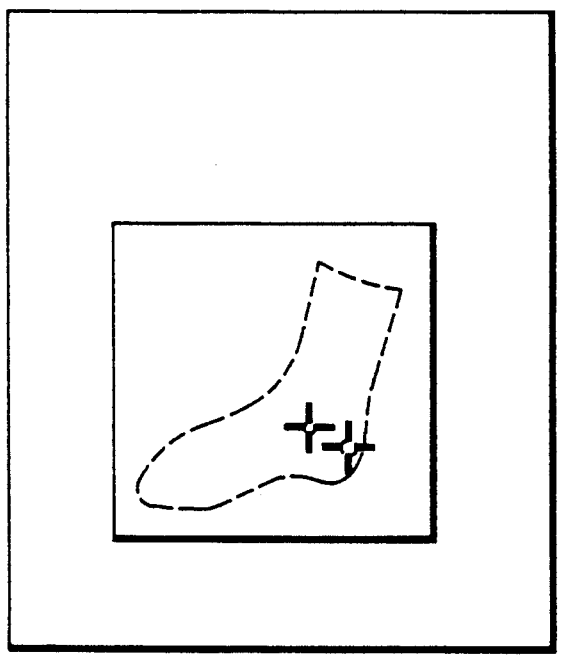
FIG. 9 is an image with superimposed hole markers.

The extreme top, bottom, right and left hand points of the object boundary are now identified from the boundary data. Starting at the lowest point, pixels within the boundary along each horizontal line in turn are examined to see if they correspond to the expected grey scale value, i.e. the binarized object value. If any pixel or pixel cluster does not so correspond, its coordinates are stored. This process is repeated in the vertical direction—FIGS. 7 and 8 show the processes in operation. Points within the boundary which are found to be inconsistent in both horizontal and vertical tests are identified as holes and a cross-wire marker is superimposed on each such hole in the displayed image as shown in FIG. 9.

This completes the process, except that, as already mentioned, an audible alarm or an automatic discarding operation to remove the garment from the line may be effected on the detection of a hole.

We claim:

1. A method for inspecting garments for holes comprising:
   front-lighting the garment against a contrasting background and forming a pixel image thereof,
   isolating garment pixels from background pixels by automatically selecting an optimum binarization threshold grey level,
   binarizing the image at that level,
   determining the garment boundary,
   testing for consistency of grey level within the garment boundary on the binarized image along rows and columns of pixels within the garment boundary and noting inconsistent pixels, and
   identifying as holes only pixels which have been noted as inconsistent in both horizontal and vertical tests.

2. A method according to claim 1, which comprises selecting the threshold grey level on the basis of data from a part of the image.

3. A method according to claim 2, which comprises using a single row or column of pixels for said data.

4. A method according to any one of claims 1 to 3, which comprises selecting the threshold grey level by thresholding the image at all possible grey levels to yield a histogram in which the number of segmented pixels is plotted against the threshold grey level, said histogram having two peak values corresponding to object and background, and taking the optimum binarization threshold grey level to be that level at which the histogram has a minimum value between the peaks.

5. A method according to claim 1, which comprises determining the garment boundary in the binarized image by tracing the boundary with an eight-directional Freeman chain code robot.

6. A method according to claim 1 which comprises comparing the length of the determined garment boundary to a predetermined minimum length to eliminate spurious measurements of noise clusters in the background.

7. A method according to claim 1, which comprises producing a fresh, binarized image for the grey level consistency testing by a low pass filter operation on the original pixel image, and binarizing said filtered image using the selected threshold grey level.

8. A method according to claim 1, which comprises indicating any inconsistent pixel group discovered within the garment boundary on a displayed image by a superimposed marker.

9. A method according to claim 1, which comprises making the pixel image by a video camera.

10. A method according to claim 1, in which the garment comprises a knitted garment.

11. A method according to claim 10, wherein the garment comprises a boarded garment.

* * * * *